United States Patent
Jäger et al.

(10) Patent No.: US 7,138,360 B2
(45) Date of Patent: Nov. 21, 2006

(54) METHOD FOR PRODUCING A SOLID HERBICIDE FORMULATION

(75) Inventors: Karl-Friedrich Jäger, Limburgerhof (DE); Cyrill Zagar, Ludwigshafen (DE)

(73) Assignee: BASF Aktiengesellschaft, Ludwigshafen (DE)

(*) Notice: Subject to any disclaimer, the term of this patent is extended or adjusted under 35 U.S.C. 154(b) by 605 days.

(21) Appl. No.: 10/362,511

(22) PCT Filed: Aug. 30, 2001

(86) PCT No.: PCT/EP01/10001

§ 371 (c)(1),
(2), (4) Date: Feb. 25, 2003

(87) PCT Pub. No.: WO02/17718

PCT Pub. Date: May 1, 2002

(65) Prior Publication Data

US 2004/0023803 A1    Feb. 5, 2004

(30) Foreign Application Priority Data

Aug. 31, 2000  (DE) ............................... 100 43 122

(51) Int. Cl.
    *A01N 25/12*   (2006.01)
    *A01N 47/36*   (2006.01)
    *A01P 13/00*   (2006.01)
(52) U.S. Cl. .................. 504/211; 504/212; 504/213; 504/214; 504/215; 504/216; 504/217; 504/367
(58) Field of Classification Search ............. 504/211, 504/212, 213, 214, 215, 216, 217, 367
See application file for complete search history.

(56) References Cited

U.S. PATENT DOCUMENTS

| | | | |
|---|---|---|---|
| 5,071,470 A | 12/1991 | Mayer et al. | |
| 5,104,441 A | 4/1992 | Hamprecht et al. | |
| 5,276,007 A | 1/1994 | Hamprecht et al. | |
| 5,478,798 A | 12/1995 | Mayer et al. | |
| 5,635,450 A | 6/1997 | Mayer et al. | |
| 6,054,410 A | 4/2000 | Landes et al. | |
| 6,242,382 B1 | 6/2001 | Bratz et al. | |

FOREIGN PATENT DOCUMENTS

| | | |
|---|---|---|
| CA | 2280513 | 8/1998 |
| DE | 40 07 683 | 9/1991 |
| EP | 124 295 | 11/1984 |
| EP | 291 851 | 11/1988 |
| EP | 313 317 | 4/1989 |
| EP | 388 873 | 9/1990 |
| EP | 554 015 | 8/1993 |
| EP | 764 404 | 3/1997 |
| WO | 92/09608 | 6/1992 |
| WO | 97/10714 | 3/1997 |
| WO | 98/34482 | 8/1998 |
| WO | 98/42192 | 10/1998 |

OTHER PUBLICATIONS

Fluorine in Agriculture, Hamprecht et al., paper 12, 1-14.
J6 2084-004 Abstract.
J6 3023 806 Abstract.
JP 08104603 Abstract.
Hay, Chemistry of Sulfonylurea Herbicides XP000202810 247-261.

*Primary Examiner*—S. Mark Clardy
(74) *Attorney, Agent, or Firm*—Novak Druce & Quigg, LLP

(57) ABSTRACT

The invention relates to a method for producing a solid herbicide formulation containing a) a herbicide from the group of sulfonylurea, or the salts thereof which are useful in the agricultural domain. b) optionally at least one other herbicide. c) optionally a safener, and d) at least one formulation adjuvant. A suspension is formed in water, consisting of the sulfonylurea a). optionally at least one other herbicide b), optionally a safener c) and at least one formulation adjuvant d). The suspension is adjusted to a pH value between 6.5 and 8 by adding an acid or a base, and is then dried to obtain the solid formulation.

12 Claims, No Drawings

METHOD FOR PRODUCING A SOLID HERBICIDE FORMULATION

The present invention relates to a process for the preparation of a solid herbicidal formulation based on sulfonylureas with or without further herbicides and with or without safeners, and formulation auxiliaries.

Herbicidally active sulfonylureas are known from the prior art, for example from EP-388 873, EP-559 814, EP-291 851 and DE-40 07 683 and from Conference Proceedings "Fluorine in Agriculture", Jan. 9–11, 1995, Manchester, Chapter "New Fluoro Intermediates for Herbicidal Sulfonylureas".

This general class of substances also includes tritosulfuron, of the formula Ia, which is an especially preferred sulfonylurea for the purposes of the solid formulation according to the invention.

Sulfonylurea-based formulations are disclosed, for example, in EP-A 0859 548 and in EP-A 0955 809.

It is known from the literature that formulations comprising sulfonylureas are problematic with regard to the stability of the active ingredients since the active ingredient may decompose over time under unfavorable conditions. The desired herbicidal action ceases to exist in such a case. The tendency to disintegrate is also problematic with regard to the registration requirements, since certain minimal requirements with regard to the stability of plant protectants in formulations are set upon registration.

JP-A 62/084004 describes the use of calcium carbonate and sodium tripolyphosphate for stabilizing sulfonylurea-comprising formulations.

JP-A 63/023806 describes a solution for the problem by using specific carriers and vegetable oils for the preparation of solid sulfonylurea-comprising formulations. JP-A 08/104,603 describes similar effects when using epoxidized natural oils. Both the abovementioned applications share the feature of incorporating vegetable oils in the solid formulation in order to exploit not only an improved stability, but also the activity-enhancing effects of these substances which act as adjuvants.

Similar effects are exploited when incorporating vegetable oils into liquid formulations (generally suspension concentrates; cf. EP-A 313317 and EP-A 554015).

The tendency of tritosulfuron, of the formula Ia, to decompose can be noticed for example by the fact that the content of active ingredient goes down or by the fact that a decomposition product such as, for example, 2-amino-4-methoxy-6-trifluoromethyltriazine (AMTT), of the formula A

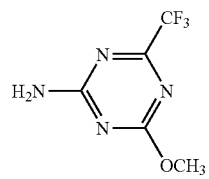

increases.

EP-A 0124 295 discloses that stable aqueous formulations of certain sulfonylureas can be obtained by adding, to aqueous suspensions of the active ingredients, agriculturally useful salts of carboxylic acids or inorganic acids whose pH is between 6 and 10. EP-A 0124 295 exclusively describes aqueous compositions.

It is an object of the present invention to provide a process for the preparation of solid formulations with sulfonylureas as active ingredients whose shelf life is markedly improved over the prior-art solid formulations.

We have found that this object is achieved according to the invention by a process for the preparation of a solid herbicidal formulation comprising
a) a herbicide from the group of the sulfonylureas or their agriculturally useful salts,
b) with or without one or more further herbicides,
c) with or without a safener,
d) one or more formulation auxiliaries, which process comprises suspending the sulfonylurea a) with or without one or more further herbicides b) and with or without a safener c) and one or more formulation auxiliaries d) in water to give a suspension, bringing the suspension to pH 6.5 to 8 by adding an acid or base and drying it to give a solid formulation.

Suitable sulfonylureas a) are, in general, compounds containing the structural unit

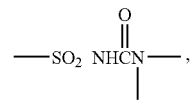

in particular the structural unit

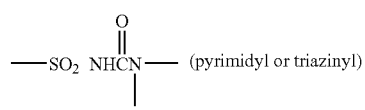

or the structural unit

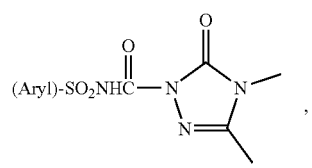

Preferred sulfonylureas which are used are those of the formula I

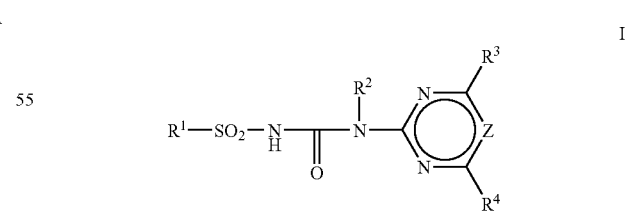

where the substituents have the following meanings:
$R^1$ is N—($C_1$–$C_4$-alkyl)-N—($C_1$–$C_4$-alkylsulfonyl)amino or an aromatic or heteroaromatic ring selected from the group consisting of phenyl, benzyl, 1H-pyrazol-5-yl, pyridin-2-yl, thiophen-3-yl and imidazo[1,2-a]pydridin-3-yl, it being possible for the aromatic ring optionally to have attached to it one to three substituents selected from the group consisting of halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkoxy-$C_1$–$C_4$-alkyl, carboxyl, $C_1$–$C_4$-alkoxycarbonyl, 3-oxetanyloxycarbonyl, aminocarbonyl, $C_1$–$C_4$-alkylaminocarbonyl, di-($C_1$–$C_4$-alkyl)aminocarbonyl, $C_1$–$C_4$-alkylsulfonyl, formylamino, $C_1$–$C_4$-alkylcarbonylamino, ($C_1$–$C_4$-alkylcarbonylamino)-$C_1$–$C_4$-alkyl, $C_1$–$C_4$-alkylsulfonylamino, ($C_1$–$C_4$-alkylsulfonylamino)-$C_1$–$C_4$-alkyl.

$R^2$ is hydrogen or methyl $R^3$ and $R^4$ independently of one another are halogen, $C_1$–$C_4$-alkyl, $C_1$–$C_4$-haloalkyl, $C_1$–$C_4$-alkoxy, $C_1$–$C_4$-haloalkoxy, amino, $C_1$–$C_4$-alkylamino, di-($C_1$–$C_4$-alkyl)amino;

Z is N, CH;

or their agriculturally useful salts.

Especially preferred sulfonylureas of the formula I are

ACC 322140;

amidosulfuron;

azimsulfuron(N-[[(4,6-dimethoxy-2-pyrimidinyl)amino]-carbonyl]-1-methyl-4-(2-methyl-2H-tetrazol-5-yl)-1H-pyrazole-5-sulfonamide);

bensulfuron-methyl(methyl 2-[[[[[(4,6-dimethoxy-2-pyrimidinyl)-amino]-carbonyl]amino]sulfonyl]methyl]benzoate);

ethyl 2-[[[[(4-chloro-6-methoxy-2-pyrimidinyl)-amino]carbonyl]amino]sulfonyl]benzoate(chlorimuron-ethyl);

2-chloro-N-[[(4-methoxy-6-methyl-1,3,5-triazin-2-yl)amino]-carbonyl]benzenesulfonamide (chlorsulfuron);

chlorsulfoxim;

cinosulfuron;

cyclosulfamuron;

ethametsulfuron-methyl(methyl 2-[[[[[4-ethoxy-6-(methylamino)-1,3,5-triazin-2-yl]amino]carbonyl]amino]sulfonyl]benzoate);

ethoxysulfuron;

flazasulfuron;

flupyrsulfuron(methyl 2-[[[[(4,6-dimethoxy-2-pyrimidinyl)-amino]-carbonyl]amino]sulfonyl]-6-(trifluoromethyl)-3-pyridinecarboxylate);

halosulfuron-methyl;

imazosulfuron;

methyl 2-[[[[(4-methoxy-6-methyl-1,3,5-triazin-2-yl)amino]-carbonyl]amino]sulfonyl]benzoate(metsulfuron-methyl);

nicosulfuron(2-[[[[(4,6-dimethoxy-2-pyrimidinyl)amino]-carbonyl]amino]sulfonyl]-N,N-dimethyl-3-pyridinecarboxamide);

oxasulfuron;

primisulfuron(methyl 2-[[[[[4,6-bis(difluoromethoxy)-2-pyrimidinyl]amino]carbonyl]amino]sulfonyl]benzoate);

prosulfuron;

pyrazosulfuron-ethyl(ethyl 5-[[[[(4,6-dimethoxy-2-pyrimidinyl)-amino]carbonyl]amino]sulfonyl]-1-methyl-1H-pyrazole-4-carboxylate);

rimsulfuron(N-[[(4,6-dimethoxy-2-pyrimidinylamino]carbonyl]-3-(ethylsulfonyl)-2-pyridinesulfonamide);

sulfosulfuron;

sulfometuron-methyl(methyl 2-[[[[(4,6-dimethyl-2-pyrimidinyl)-amino]carbonyl]amino]sulfonyl]benzoate);

thifensulfuron-methyl(methyl-3-[[[[(4-methoxy-6-methyl-1,3,5-triazin-2-yl)amino]carbonyl]amino]sulfonyl]-2-thiophene-carboxylate);

2-(2-chloroethoxy)-N-[[(4-methoxy-6-methyl-1,3,5-triazin-2-yl)-amino]carbonyl]benzenesulfonamide(triasulfuron);

tribenuron-methyl(methyl 2-[[[[N-(4-methoxy-6-methyl-1,3,5-triazin-2-yl)-N-methylamino]carbonyl]amino]sulfonyl]benzoate);

triflusulfuron-methyl(methyl 2-[[[[[4-(dimethylamino)-6-(2,2,2-trifluoroethoxy)-1,3,5-triazin-2-yl]amino]carbonyl]amino]-sulfonyl]-3-methylbenzoate) and tritosulfuron (N[[[4-methoxy-6-(trifluoromethyl)-1,3,5-triazin-2-yl]amino]carbonyl]-2-(trifluoromethyl)benzenesulfonamide), of the formula Ia

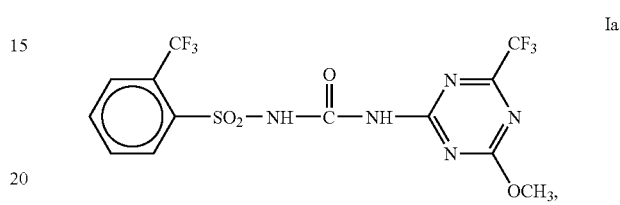

and the sodium salt of tritosulfuron(N-[[[4-methoxy-6(trifluoromethyl)-1,3,5-triazin-2-yl]amino]carbonyl]-2-(trifluoromethyl)benzenesulfonamide, monosodium salt), of the formula Ia'

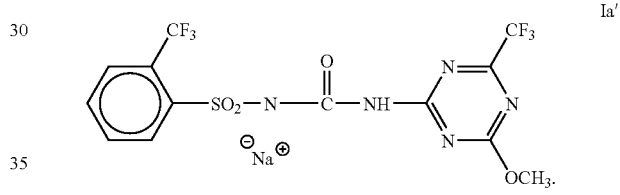

Tritosulfuron and the sodium salt of tritosulfuron are especially preferred.

The sulfonylureas a) or their agriculturally useful salts amount to between 0.5 and 85% by weight, preferably between 25 and 75% by weight, based on the solid formulation.

The process according to the invention may be carried out with or without the concomitant use of one or more further herbicides b). Examples of suitable herbicides b) are cinidon-ethyl, florasulam, flucarbazone, procarbazone, bentazone, dicamba, MCPA, mecoprop-P, clefoxidim, cycloxidim and their agriculturally useful salts.

Especially preferred are cinidon-ethyl, flucarbazone, procarbazone and dicamba.

The concomitant use of the herbicides b) is optional. If they are used concomitantly, they, or their agriculturally useful salts, amount to between 0.5 and 75% by weight based on the solid formulation.

The process according to the invention may also be carried out with or without the concomitant use of a safener c). Examples of suitable safeners c) are cloquintocet, cloquintocet-mexyl, dicyclonon, furilazole, fenchlorazole, fenchlorazol-ethyl, mefenpyr, mefenpyr-diethyl, isoxadifen, isoxadifen-ethyl and their agriculturally useful salts.

Especially preferred are dicyclonon, isoxadifen and isoxadifen-ethyl.

The concomitant use of the safener c) is optional. If they are used concomitantly, they or their agriculturally useful salts, amount to between 0.5 and 50% by weight, based on the solid formulation.

In addition to the above-described components a), b) and c), formulation auxiliaries are also used concomitantly in the process according to the invention in an amount of from 15 to 99.5% by weight.

Surfactants which are suitable in this context are the alkali metal salts, alkaline earth metal salts or ammonium salts of aromatic sulfonic acids, for example lignosulfonic acid, phenolsulfonic acid, naphthalenesulfonic acid and dibutylnaphthalenesulfonic acid, and of fatty acids; alkyl polyglycosides, condensates of sulfonated naphthalene and its derivatives with formaldehyde, condensates of naphthalene or of the naphthalenesulfonic acids with phenol and formaldehyde, condensates of phenol or of phenolsulfonic acid with formaldehyde, condensates of phenol with formaldehyde and sodium sulfite, polyoxyethylene octylphenyl ether, ethoxylated isooctyl-, octyl- or nonylphenol, tributylphenyl polyglycol ether, alkylaryl polyether alcohols, isotridecyl alcohol, fatty alcohol/ethylene oxide condensates, ethoxylated castor oil, polyoxyethylene alkyl ethers, ethoxylated triarylphenols, salts of phosphated triarylphenol ethoxylates, polyoxypropylene alkyl ethers, lauryl alcohol polyglycol ether acetate, sorbitol esters, lignin-sulfite waste liquors or methylcellulose, or mixtures of these.

When surfactants are concomitantly used, they generally amount to a range of from 0.5 to 50% by weight, based on the total weight of the solid mixture.

Carriers which are suitable are, for example, mineral earths such as silicas, silica gels, silicates, talc, kaolin, attaclay, limestone, chalk, loess, clay, dolomite, diatomaceous earth, calcium sulfate, magnesium sulfate, magnesium oxide, ground synthetic materials, fertilizers such as ammonium sulfate, ammonium phosphate, ammonium nitrate, thiourea and urea, products of vegetable origin such as cereal meals, tree bark meal, wood meal and nutshell meal, cellulose powders, attapulgites, montmorillonites, micas, vermiculites, synthetic silicas and synthetic calcium silicates, or mixtures of these.

The following may be employed as further additives in amounts which are customary per se:

Binders such as:

polyvinylpyrrolidone, polyvinyl alcohol, partially hydrolyzed polyvinyl acetate, carboxymethylcellulose, starch, vinylpyrrolidone/vinyl acetate copolymers and polyvinyl acetate, or mixtures of these;

antifoams such as:

silicone emulsions, long-chain alcohols, phosphoric esters, acetylenediols, fatty acids or organofluorine compounds, and complexing agents such as:

salts of ethylenediaminetetraacetic acid (EDTA), salts of trinitrilolriacetic acid or salts of polyphosphoric acids, or mixtures of these.

In the process according to the invention, the sulfonylurea a) with or without one or more herbicides b) and with or without a safener c), and one or more formulation auxiliaries d), is suspended in water to give a suspension, and the suspension is brought to pH 6.5 to 8 by addition of an acid or base and dried to give a solid formulation.

The suspension is prepared in a stirred vessel by stirring the components and grinding the mixture in a bead mill.

The resulting suspension is brought to pH 6.5 to 8 by addition of an acid or base. It is preferred to bring it to a pH of 6.5 to 7.5, especially preferably a pH of 6.8 to 7.2.

Suitable acids are inorganic and organic acids such as, for example, sulfuric acid, hydrochloric acid or p-toluenesulfonic acid.

Suitable bases are alkali metal hydroxides, alkaline earth metal hydroxides, ammonia and amines. NaOH is preferably used.

The solid formulations can be prepared from the resulting suspension by a plurality of processes.

Preferred methods for the preparation of the abovementioned solid formulations are spray-drying and fluidized-bed agglomeration.

Fluidized-bed granulation (FBG) is especially suitable. Depending on the desired composition of the solid formulation, the suspension which comprises all components of the formula is atomized and agglomerated in an FBG apparatus.

In general, the granules are dried sufficiently during fluidized-bed granulation. However, it may be advantageous to follow the granulation step by a separate drying step in the same dryer or in a separate dryer. Following granulation/drying, the product is cooled and screened.

A suitable granulation liquid is water. Also suitable are aqueous solutions of inorganic salts, nonionic surfactants, anionic surfactants, solutions of binders such as polyvinylpyrrolidone, polyvinyl alcohol, carboxymethylcellulose, starch, vinylpyrrolidine/vinyl acetate copolymers, sugars, dextrin or polyethylene glycol.

The solid formulations prepared by the process according to the invention can be prepared in the form of powders, granules, briquettes, tablets and similar formulation variants. Especially preferred, in addition to powders, are granules. The powders may take the form of water-soluble or water-dispersible powders. The granules may take the form of water-soluble or water-dispersible granules for use in spray application, or else, for direct application, what are known as granules for spreading. The mean particle size of the granules is generally between 200 µm and 2 mm.

The resulting granule formulations are dust-free, free-flowing, non-caking products which are readily soluble or dispersible in cold water.

Owing to their properties, the products can be packaged readily in larger amounts. They can be handled in containers such as bags or sacks made of plastic, paper or laminate or else in cardboard boxes or other bulk containers. To avoid further exposure of the user it is possible to package the products in water-soluble film bags such as, for example, bags made of polyvinyl alcohol film, and these film bags are placed directly in the spray tank, where they dissolve. Materials which can be employed for such water-soluble films are, inter alia, polyvinyl alcohol or cellulose derivatives such as methylcellulose, methylhydroxypropylcellulose or carboxymethylcellulose. Since the product is portioned into quantities which match the intended use, it no longer comes into contact with the user. The water-soluble bags are preferably packaged in an external shell which is impermeable to steam, such as a polyethylene film, polyethylene/paper laminate or aluminum foil.

The solid formulations prepared by the process according to the invention are storage-stable. In accordance with a storage test laid down by the authorization authorities, they are stored for 14 days at 54° C. The decrease in the active ingredient content can be determined for example in the case of tritosulfuron by the increasing content of the degradation product AMTT, which can be measured with great sensitivity.

The table hereinbelow illustrates the components employed in the examples.

TABLE 1

| Name | Chemical name | Supplied by |
|---|---|---|
| Tamol ® NH | naphthalenesulfonic acid/formaldehyde condensate | BASF AG |
| Ufoxane ® 3A | sodium lignosulfonate | Borregaard |
| Antischaummittel SRE ® | silicone oil emulsion | Wacker-Chemie |
| Reax ® 88 A | sodium lignosulfonate | Westvaco |

PROCESS EXAMPLES

Example 1

A mixture composed of
1100 g of distilled water,
7.6 g of Antischaummittel SRE,
212.5 g of Reax 88 A and
653 g of technical-grade tritosulfuron was mixed and the mixture was ground in a bead mill. The resulting suspension was brought to the desired pH of 5.1, 6, 7, 8 and 9 using aqueous sodium hydroxide solution (25% strength). Thereupon, the suspension was applied to Petri dishes and dried in a vacuum drying oven at a drying temperature of 70° C. The dried coating was scraped from the Petri dish with the aid of a scraper and passed through a 0.5 mm sieve. The fines were separated by means of a 0.1 mm sieve. The product obtained was tested for the stability of the active ingredient.

Example 2

A mixture composed of
203.2 g of technical-grade tritosulfuron,
122.3 g of technical-grade flucarbazone-sodium,
4 g of Antischaummittel SRE,
55.1 g of Tamol NH,
110.2 g of Ufoxane 3A and
650 g of distilled water was mixed and ground in a bead mill. The resulting suspension was brought to the desired pH of 6.5 and 7.0 with aqueous sodium hydroxide solution (25% strength). Thereupon, the suspension was applied to Petri dishes and dried in a vacuum drying oven at a drying temperature of 70° C. The dried coating was scraped from the Petri dish with the aid of a scraper and passed through a 0.5 mm sieve. The fines were separated by means of a 0.1 mm sieve. The product obtained was tested for the stability of the active ingredient.

Example 3

A mixture composed of
101.6 g of tritosulfuron,
528.6 g of technical-grade dicamba,
6.4 g of Antischaumemulsion SRE,
102.7 g of Reax 88A and
637.9 g of distilled water was mixed in a stirred vessel. First, the water and Reax 88A were introduced, and the container was charged with the dicamba. By addition of aqueous sodium hydroxide solution (25% strength), the dicamba was reacted to give a solution. Thereupon, the remaining constituents were admixed, and the suspension was ground in a bead mill.

The resulting suspension was brought to the desired pH of 6, 7, 8 and 9 with aqueous sodium hydroxide solution (25% strength). Thereupon, the suspension was applied to Petri dishes and dried in a vacuum drying oven at a drying temperature of 70° C. The dried coating was scraped from the Petri dish with the aid of a scraper and passed through a 0.5 mm sieve. The fines were separated by means of a 0.2 mm sieve. The product obtained was tested for the stability of the active ingredient.

Test Methods

The active ingredient content and the AMTT content of the formulations were each determined by means of quantitative HPLC. To test the storage stability, samples of the formulation in question in accordance with Examples 1–3 were stored for 14 days in tightly sealed glass containers at 54° C. The samples were then analyzed and compared with the comparative value at the beginning of the storage (zero value). The active ingredient content is shown in each case as relative quantity based on the zero value (as a percentage). The storage experiments were carried out following the method CIPAC MT 46. The shelf life of a product is estimated by short-term storage at elevated temperature.

TABLE 2

| Example 1 | | Preparation | Storage 14 days, | |
|---|---|---|---|---|
| pH of the suspension | Active ingredients | Concentration % by weight | 54° C. % by weight | Notes |
| 5.1 | tritosulfuron | 74.2 | 99.3 (rel.) | |
|  | AMTT | 0.03 | 0.249 | |
| 6 | tritosulfuron | 72.3 | 99.9 (rel.) | |
|  | AMTT | 0.03 | 0.250 | |
| 7 | tritosulfuron | 71.7 | 100.8 (rel.) | |
|  | AMTT | 0.033 | 0.178 | |
| 8 | tritosulfuron | 67.5 | 100.5 (rel.) | suspension is highly viscous |
|  | AMTT | 0.026 | 0.056 | |
| 9 | tritosulfuron | 72.4 | 97.7 (rel.) | suspension is highly viscous |
|  | AMTT | 0.035 | 0.234 | |

TABLE 3

| Example 3 | | Preparation | Storage 14 days, | |
|---|---|---|---|---|
| pH of the suspension | Active ingredients | Concentration % by weight | 54° C. % by weight | Notes |
| 6.5 | tritosulfuron | 40.5 | 98.8 (rel.) | |
|  | AMTT | 0.025 | 0.164 | |
|  | flucarbazone-sodium | 24.1 | 98.8 (rel.) | |
| 7.0 | tritosulfuron | 41.1 | 100 (rel.) | |
|  | AMTT | 0.019 | 0.065 | |
|  | flucarbazone-sodium | 24.3 | 99.5 (rel.) | |

TABLE 4

| Example 4 | | Preparation | Storage 14 days, | |
|---|---|---|---|---|
| pH of the suspension | Active ingredient | Concentration % by weight | 54° C. % by weight | Notes |
| 6 | tritosulfuron | 11.9 | 91.3 (rel.) | |
|  | AMTT | 0.009 | 0.470 | |

TABLE 4-continued

| Example 4 | Preparation | | Storage 14 days, | |
|---|---|---|---|---|
| pH of the suspension | Active ingredient | Concentration % by weight | 54° C. % by weight | Notes |
| 7 | dicamba | 60.4 | 100 (rel.) | |
|   | tritosulfuron | 11.9 | 99.7 (rel.) | |
|   | AMTT | 0.007 | 0.011 | |
| 8 | dicamba | 58.7 | 100 (rel.) | suspension turns highly viscous |
|   | tritosulfuron | 11.3 | 98.8 (rel.) | |
|   | AMTT | 0.007 | 0.007 | |
| 9 | dicamba | 58.5 | 100 (rel.) | suspension turns highly viscous |
|   | tritosulfuron | 10.4 | 102.6 (rel.) | |
|   | AMTT | 0.006 | 0.007 | |
|   | dicamba | 58.0 | 101.9 (rel.) | |

The data of Tables 2 to 4 show clearly that the solid formulations prepared by the process according to the invention are storage-stable when the pH of the suspension is above 6. From pH 8, the suspension turns highly viscous so that further processing is made difficult.

We claim:

1. A process for the preparation of a solid herbicidal formulation comprising
   a) a herbicide from the group of the sulfonylureas or their agriculturally useful salts,
   b) with or without one or more further herbicides,
   c) with or without a safener,
   d) one or more formulation auxiliaries,
   which process comprises suspending the sulfonylurea a) with or without one or more further herbicides b) and with or without a safener c) and one or more formulation auxiliaries d) in water to give a suspension, bringing the suspension to pH 6.5 to 8 by adding an acid or base and drying it to give a solid formulation.

2. A process as claimed in claim 1, wherein the herbicide a) used as a sulfonylurea of the formula I

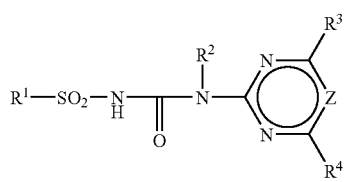

I where the substituents have the following meanings:
R$^1$ is N—(C$_1$–C$_4$-alkyl)-N—(C$_1$–C$_4$-alkylsulfonyl)amino or an aromatic or heteroaromatic ring selected from the group consisting of phenyl, benzyl, 1H-pyrazol-5-yl, pyridin-2-yl, thiophen-3-yl and imidazol[1,2-a]pydridin-3-yl, it being possible for the aromatic ring optionally to have attached to it one to three substituents selected from the group consisting of halogen, C$_1$–C$_4$-alkyl, C$_1$–C$_4$-haloalkyl, C$_1$–C$_4$-alkoxy, C$_1$–C$_4$-haloalkoxy, C$_1$–C$_4$-alkoxy-C$_1$–C$_4$-alkyl, carboxyl, C$_1$–C$_4$-alkoxycarbonyl, 3-oxetanyloxycarbonyl, aminocarbonyl, C$_1$–C$_4$-alkylaminocarbonyl, di-(C$_1$–C$_4$-alkyl)aminocarbonyl, C$_1$–C$_4$-alkylsulfonyl, formylamino, C$_1$–C$_4$-alkylcarbonylamino, (C$_1$–C$_4$-alkylcarbonylamino)-C$_1$–C$_4$-alkyl, C$_1$–C$_4$-alkylsulfonylamino, (C$_1$–C$_4$-alkylsulfonylamino)-C$_1$–C$_4$-alkyl;

R$^2$ is hydrogen or methyl;
R$^3$ and R$^4$ independently of one another are halogen, C$_1$–C$_4$-alkyl, C$_1$–C$_4$-haloalkyl, C$_1$–C$_4$-alkoxy, C$_1$–C$_4$-haloalkoxy, amino, C$_1$–C$_4$-alkylamino, di-(C$_1$–C$_4$-alkyl)amino;
Z is N, CH;
or their agriculturally useful salts.

3. A process as claimed in claim 1, wherein the herbicide a) used is a sulfonylurea selected from the group consisting of tritosulfuron, bensulfuron-methyl, chlorimuron-ethyl, chlorsulfuron, cinosulfuron, halosulfuron-methyl, ethametsulfuron-methyl, flazasulfuron, imazosulfuron, metsulfuron-methyl, nicosulfuron, primisulfuron-methyl, pyrazosulfuron-ethyl, rimsulfuron, sulfometuron-methyl, thifensulfuron-methyl, triasulfuron, tribenuron-methyl, triflusulfuron-methyl, prosulfuron, ethoxysulfuron, azimsulfuron, oxasulfuron, sulfosulfuron, iodosulfuron, foramsulfuron, trifloxysulfuron, amidosulfuron, mesosulfuron, flupyrsulfuron-methyl, iodosulfuron-methyl and their agriculturally useful salts.

4. A process as claimed in claim 3, wherein the herbicide a) used is tritosulfuron or one of its agriculturally useful salts.

5. A process as claimed in claim 1, wherein a herbicide b) is used which is selected from the group consisting of cinidon-ethyl, florasulam, flucarbazon, procarbazon, netazon, dicamba, MCPA, mecoprop-P, clefoxidim, cycloxidim and their agriculturally useful salts.

6. A process as claimed in claim 1, wherein a safener c) is used which is selected from the group consisting of cloquintocet-mexyl, dicyclonon, furilazole, fenchlorazole, fenchlorazole-ethyl, mefenpyr, mefenpyr-diethyl, isoxadifen, isoxadifen-ethyl and their agriculturally useful salts.

7. A process as claimed in claim 1, wherein the formulation auxiliary d) used is a solid carrier.

8. A process as claimed in claim 1, wherein the formulation auxiliary d) used is a surfactant.

9. A process as claimed in claim 1, wherein
   0.5 to 85% by weight of the sulfonylurea a)
   0 to 75% by weight of the herbicide b),
   0 to 50% by weight of the safener c) and
   10 to 99.5% by weight of the formulation auxiliariy/auxiliaries d) are used.

10. A process as claimed in claim 1, wherein the suspension is brought to pH 6.5 to 7.5.

11. A process as claimed in claim 1, wherein the suspension is brought to a pH of 6.8 to 7.2.

12. A process for controlling harmful plants which comprises
    i) providing a solid herbicidal formulation comprising
       a) a herbicide from the group of the sulfonylureas or their agriculturally useful salts,
       b) with or without one or more further herbicides,
       c) with or without a safener,
       d) one or more formulation auxiliaries,
       by the process defined in claim 1, and
    ii) applying an effective amount of the solid formulation, or of an aqueous solution or dispersion thereof, to the plants or their habitat.

* * * * *

UNITED STATES PATENT AND TRADEMARK OFFICE
CERTIFICATE OF CORRECTION

| | | |
|---|---|---|
| PATENT NO. | : 7,138,360 B2 | |
| APPLICATION NO. | : 10/362511 | |
| DATED | : November 21, 2006 | |
| INVENTOR(S) | : Jäger et al. | |

It is certified that error appears in the above-identified patent and that said Letters Patent is hereby corrected as shown below:

claim 3, column 10, indicated line 20, "foramsulfu-" should read --formasulfu- --

Signed and Sealed this

Twenty-second Day of May, 2007

JON W. DUDAS
*Director of the United States Patent and Trademark Office*